(12) United States Patent
Chu

(10) Patent No.: US 7,024,718 B2
(45) Date of Patent: Apr. 11, 2006

(54) ELECTRIC TOOTHBRUSH MECHANISM

(76) Inventor: J Y Chu, Flat A, 12th Floor, Block 4, Greenpark Villa, 9, Kut Cheung Crescent, Sheung Shui, New Territories (HK)

( * ) Notice: Subject to any disclaimer, the term of this patent is extended or adjusted under 35 U.S.C. 154(b) by 332 days.

(21) Appl. No.: 10/209,929

(22) Filed: Aug. 2, 2002

(65) Prior Publication Data
US 2004/0019987 A1 Feb. 5, 2004

(51) Int. Cl.
*A46B 13/02* (2006.01)
*A61C 17/34* (2006.01)

(52) U.S. Cl. ............... 15/22.2; 15/22.1; 15/28; 15/167.1; 15/201

(58) Field of Classification Search ........ 15/22.1, 15/22.2, 28, 167.1, 201
See application file for complete search history.

(56) References Cited

U.S. PATENT DOCUMENTS

| 5,732,432 A | 3/1998 | Hui |
| 5,974,613 A | 11/1999 | Herzog |
| 6,725,490 B1 * | 4/2004 | Blaustein et al. ........... 15/22.2 |
| 2003/0084527 A1 * | 5/2003 | Brown et al. ............... 15/22.1 |

FOREIGN PATENT DOCUMENTS

| CN | 1056744 | 9/2000 |
| GB | 2 317 555 | 1/1998 |

* cited by examiner

*Primary Examiner*—Randall Chin
(74) *Attorney, Agent, or Firm*—Leydig, Voit & Mayer, Ltd.

(57) ABSTRACT

A brushing head can be attached to or formed integrally with an electric toothbrush handle. The brushing head includes a casing, a rotary drive shaft extending within the casing and having a radially offset crank portion. A linear guide track extends in a direction across the drive shaft. A tuft block is mounted to the casing and interacts with the offset crank portion and the guide track to reciprocate linearly upon rotation of the drive shaft.

4 Claims, 5 Drawing Sheets

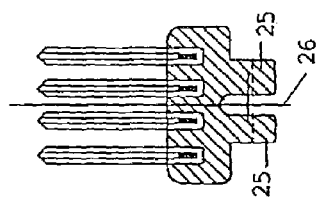
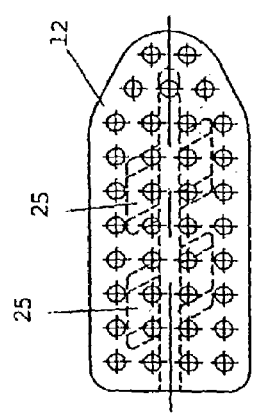
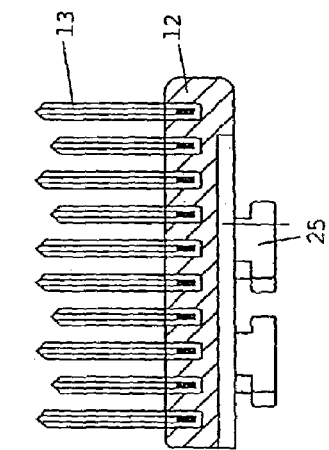
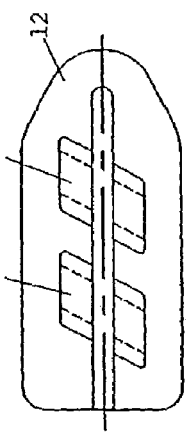
FIGURE 13
FIGURE 14
FIGURE 15
FIGURE 16

ELECTRIC TOOTHBRUSH MECHANISM

BACKGROUND OF THE INVENTION

The present invention relates to electric toothbrush mechanisms. More particularly, although not exclusively, the invention relates to a replaceable brushing attachment for an electric toothbrush, having a tuft block that is moved reciprocally by a rotating crankshaft.

There are many known electric toothbrush mechanisms having pivotally oscillating tuft blocks. Some such mechanisms are known to include a pivotally oscillating circular tuft block that oscillates back and forth about an axis that extends parallel to the bristles. The centre-most bristles of such tuft blocks provide little, if any cleaning action.

Other electric toothbrushes are known, which comprise a bristle head that moves reciprocally back and forth in a direction parallel to the longitudinal axis of the toothbrush. Such a toothbrush is disclosed in U.S. Pat. No. 4,995,131. This type of bristle movement has been criticised as being inefficient, as the bristle tips move along the gum line, instead of across the gum line.

U.S. Pat. Nos. 4,149,291 and 5,253,382 each disclose electric toothbrush mechanisms having a pivotally oscillating brushing head. In these arrangements, the entire neck of the toothbrush and the brush head itself must pivot back and forth about a pivot axis. These devices are cumbersome, inefficient and uncomfortable to use.

OBJECTS OF THE INVENTION

It is an object of the present invention to overcome or substantially ameliorate at least one of the above disadvantages and/or more generally to provide an improved electric toothbrush mechanism.

It is a further object of the present invention to provide an electric toothbrush with a tuft block that reciprocates in a linear manner substantially across the gum line, wherein all of the bristles move to provide an efficient cleaning action.

DISCLOSURE OF THE INVENTION

There is disclosed herein a brushing head attached to or formed integrally with an electric toothbrush handle, comprising:
  a casing,
  a rotary drive shaft extending within the casing and comprising a radially offset crank portion,
  a linear guide track extending in a direction across the drive shaft,
  a tuft block mounted to the casing and interacting with the offset crank portion and the guide track to reciprocate linearly upon rotation of the drive shaft.

Preferably the tuft block includes a slider received by the guide track.

Preferably the guide track and slider each have a cross-sectional shape comprising a stem and a flange, and wherein the stem of the slider is received within the stem of the guide track and the flange of the slider is received within the flange of the guide track.

Preferably the guide track extends in a direction that is at right angles with respect to the longitudinal extent of the drive shaft.

Alternatively, the guide track extends in a direction that is at an acute angle with respect to the longitudinal extent of the drive shaft.

Preferably the casing includes a neck through which the drive shaft extends.

Preferably the brushing head is a disposable attachment for a toothbrush handle within which there is located a battery and a motor having an output coupling, the attachment comprising an input coupling for engagement with the output coupling.

Preferably the casing is formed integrally with a toothbrush handle within which there is located a battery and a motor coupled to the drive shaft.

BRIEF DESCRIPTION OF THE DRAWINGS

Preferred forms of the present invention will now be described by way of example with reference to the accompanying drawings, wherein:

FIG. 13 is a schematic plan view of an alternative tuft block, FIG. 14 is a schematic cross-sectional elevational view of the tuft block of FIG. 13, FIG. 15 is a schematic cross-sectional end the elevation of view of the tuft block of FIG. 14, and FIG. 16 is a schematic inverted plan view of the tuft block of FIG. 13.

DESCRIPTION OF THE PREFERRED EMBODIMENTS

Figure 1:
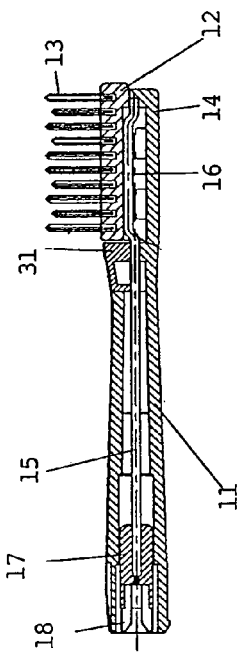
FIG. 1 is a schematic cross-sectional elevational view of a disposable attachment and a handle, forming an electric toothbrush.
Figure 3:
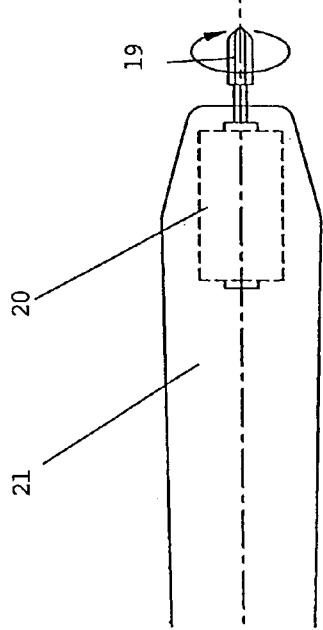
FIG. 3 is a schematic cross-sectional end elevation will view of the head portion of the attachment of FIGS. 1 and 2.
Figure 5:
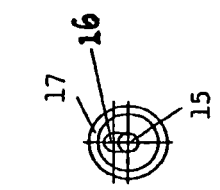
FIG. 5 is a schematic in the elevational view of the drive shaft and input coupling of FIG. 4.
Figure 4:
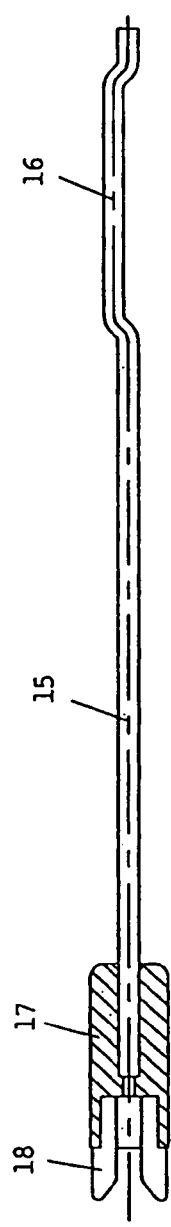
FIG. 4 is a schematic elevational view of a drive shaft and input coupling.
Figure 7:
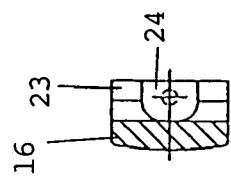
Figure 6:
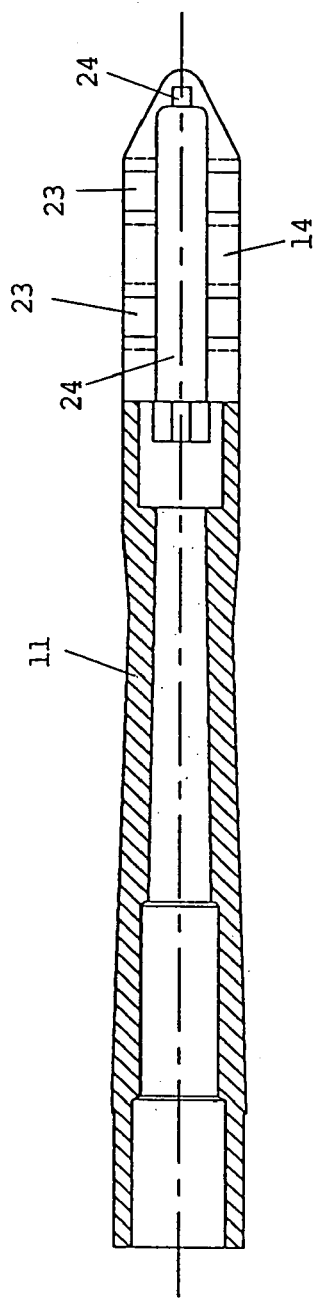
FIG. 6 is a schematic cross-sectional plan view of the casing of the attachment.
Figure 8:
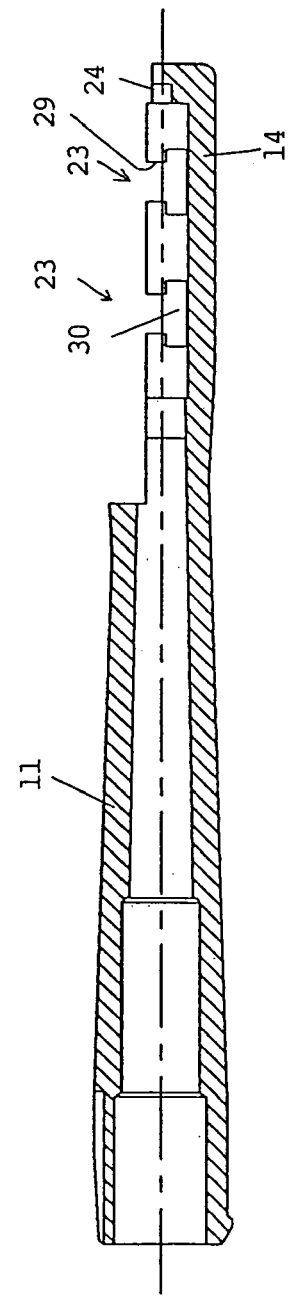
FIG. 8 is a schematic cross-sectional elevational view of the casing.
Figure 11:
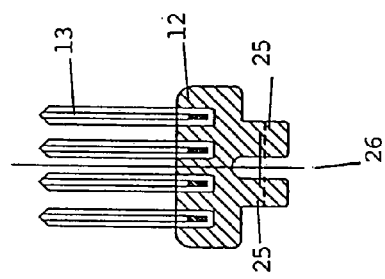
FIG. 11 is a schematic cross-sectional end elevational view of the tuft block.
Figure 9:
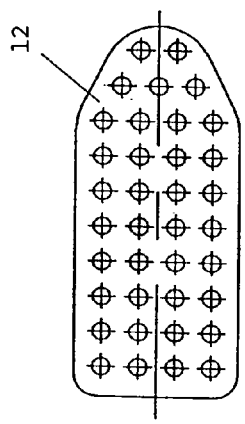
FIG. 9 is a schematic plan view of a tuft block.
Figure 10:
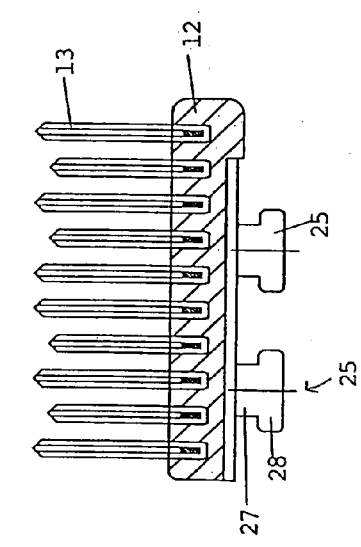
FIG. 10 is a schematic cross-sectional elevational view of the tuft block of FIG. 9.
Figure 12:
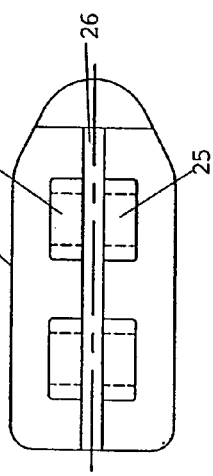
FIG. 12 is a schematic inverted plan view of the tuft to block.

In FIG. 1 of the accompanying drawings there is schematically depicted an electric toothbrush comprising a handle 22 and a replaceable brushing head attachment 10. Handle 22 has located therein a battery compartment 21 and an electric motor 20. The electric motor 20 receives current from one or more batteries within the compartment 21 via a switch (not shown). There is an output coupling 19 upon the output shaft of the motor 20. The output coupling 19 rotates as shown. The handle 22 is typically fabricated from moulded plastics material.

The replacement bristle head attachment 10, also typically fabricated from moulded plastics material, includes a casing 14 comprising a neck portion 11. A drive shaft 15 extends through the neck portion 11 and includes an offset crank portion 16 located within the casing directly beneath a tuft block 12 from which bristle tufts 13 extend. There is a bushing piece 31 attached to the casing 14 and against which the drive shaft 15 bears.

At the proximal end of the neck 11, there is an input coupling 18 and a bushing 17. The coupling 18 and bushing 17 are attached to the drive shaft 15 to effect rotation thereof upon activation of motor 20. This is because output coupling 19 is inserted into the input coupling 18.

Figure 2:
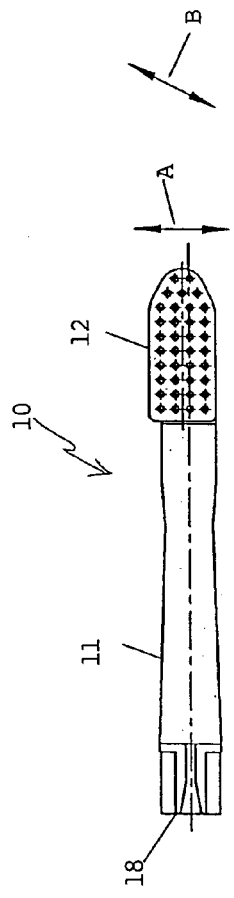
FIG. 2 is a schematic plan view of the attachment of FIG. 1.

The tuft block 12, depending on its configuration to be described later, is intended to move linearly and reciprocally in the directions indicated either by double-ended arrow A or double-ended arrow B in FIG. 2.

In order to achieve reciprocal movement in the direction indicated by double-ended arrow A, the casing 14, just beneath the tuft block 12, comprises a pair of transversely extending guide tracks 23. Each guide track includes a stem portion 29 and a flange portion 30. The tuft block accompanying this casing is depicted in FIGS. 9 to 12. The tuft block includes four individual sliders 25, transverse linear pairs of which are received within respective guide ones of the tracks 23. In between each pair of sliders, there is a slot 26 within which the crank portion 16 of the drive shaft 15 is received. Each slider 25 includes a stem 27 and a flange 28 to be received within the correspondingly-named parts of the respective guide tracks 23. As the crank 16 rotates about the longitudinal axis of the drive shaft 15, it interacts with the mutually facing faces of the sliders 25 to cause movement of the tuft block 12 transversely across the brushing head attachment as shown by the double-ended arrow A in FIG. 2.

In the alternative tuft block as depicted in FIGS. 13 to 16, the sliders 25 extend across the tuft block 12 at an acute angle with respect to the longitudinal axis of the drive shaft 15. The guide tracks in the casing 14 also extend at the same acute angle, such that upon rotation of the crank portion 16 about the longitudinal axis 15, the tuft block is caused to reciprocate in the directions indicated by double-ended arrow B in FIG. 2.

It should be appreciated that modifications and alterations obvious to those skilled in the art are not to be considered as beyond the scope of the present invention. For example, a bearing surface separate to the inwardly facing faces of the sliders might be provided for engagement with the crank portion of the drive shaft.

What is claimed is:

1. A brushing head attached to or formed integrally with an electric toothbrush handle, comprising:
   a casing,
   a rotary drive shaft extending within the casing and comprising a radially offset crank portion,
   a linear guide track extending in a direction across the drive shaft and at an acute angle with respect to the longitudinal extent of the drive shaft,
   a tuft block mounted to the casing and interacting with the offset crank portion and the guide track to reciprocate linearly upon rotation of the drive shaft, wherein the tuft block includes a slider received by the guide track, and the guide track and slider each have a cross-sectional shape comprising a stem and a flange, and
   wherein the stem of the slider is received within the stem of the guide track and the flange of the slider is received within the flange of the guide track.

2. The brushing head of claim 1, wherein the casing includes a neck through which the drive shaft extends.

3. The brushing head of claim 1, further comprising an electric toothbrush handle within which there is located a battery and a motor having an output coupling, wherein the brushing head comprises a disposable attachment attached to the electric toothbrush handle, the disposable attachment comprising an input coupling for engagement with the output coupling.

4. The brushing head of claim 1, further comprising an electric toothbrush handle within which there is located a battery and a motor coupled to the drive shaft, wherein the casing is formed integrally with the electric toothbrush handle.

* * * * *